US009005957B2

(12) United States Patent
Hong et al.

(10) Patent No.: US 9,005,957 B2
(45) Date of Patent: Apr. 14, 2015

(54) CORYNEBACTERIUM GENUS MICROORGANISM HAVING ABILITY TO PRODUCE N-ACETYL GLUCOSAMINE AND METHOD FOR PRODUCING N-ACETYL GLUCOSAMINE OR GLUCOSAMINE USING THE SAME

(75) Inventors: Kuk-Ki Hong, Seoul (KR); Jin-Su Chung, Yongin-si (KR); Sooan Shin, Seoul (KR); Hyeran Park, Incheon (KR); Jaehyun Jo, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 1029 days.

(21) Appl. No.: 13/125,181

(22) PCT Filed: Oct. 20, 2009

(86) PCT No.: PCT/KR2009/006063
§ 371 (c)(1),
(2), (4) Date: Jun. 26, 2011

(87) PCT Pub. No.: WO2010/047516
PCT Pub. Date: Apr. 29, 2010

(65) Prior Publication Data
US 2011/0250647 A1 Oct. 13, 2011

(30) Foreign Application Priority Data
Oct. 20, 2008 (KR) ........................ 10-2008-0102633

(51) Int. Cl.
C12N 9/78 (2006.01)
C12N 9/10 (2006.01)
C12P 19/26 (2006.01)

(52) U.S. Cl.
CPC ............... *C12N 9/78* (2013.01); *C12N 9/1029* (2013.01); *C12P 19/26* (2013.01)

(58) Field of Classification Search
None
See application file for complete search history.

(56) References Cited

U.S. PATENT DOCUMENTS

| 7,332,304 B2 | 2/2008 | Deng et al. |
| 2002/0160459 A1 | 10/2002 | Berry et al. |
| 2005/0003478 A1 | 1/2005 | Endo et al. |
| 2005/0042735 A1 | 2/2005 | Deng et al. |
| 2006/0094085 A1 | 5/2006 | Berry et al. |
| 2007/0269872 A1 | 11/2007 | Taguchi et al. |

FOREIGN PATENT DOCUMENTS

| JP | 2006-508643 A | 3/2006 |
| JP | 2007-514425 A | 6/2007 |
| JP | 2008-245633 A | 10/2008 |
| KR | 10-2005-0053534 A | 6/2005 |
| KR | 10-2008-0025355 A | 3/2008 |
| WO | WO 02/066667 A1 | 8/2002 |
| WO | WO 2004/003175 A2 | 1/2004 |

OTHER PUBLICATIONS

Becker, J., et al., "Amplified Expression of Fructose 1,6-Bisphosphatase in *Corynebacterium glutamicum* Increases In Vivo Flux through the Pentose Phosphate Pathway and Lysine Production on Different Carbon Sources," *Applied and Environmental Microbiology* 71(12):8587-596, American Society for Microbiology (2005).

Deng, M-D., et al., "Metabolic engineering of *Escherichia coli* for industrial production of glucosamine and N-acetylglucosamine," *Metabolic Engineering* 7:201-14, Elsevier Inc., United States (2005).

Eikmanns, B.J., et al., "A family of *Corynebacterium glutamicum/Escherichia coli* shuttle vectors for cloning, controlled gene expression, and promoter probing," *Gene* 102:93-98, Elsevier Science Publishers B.V., Netherlands (1991).

Srivastava, P., et al., "Gene expression systems in corynebacteria." *Protein Expression and Purification* 40:221-29, Elsevier Inc., United States (2005).

English language Abstact of Japanese Patent Publication No. 2008-245633 A, Japanese Patent Office, Patent & Utility Model Gazette DB, Patent Abstract of Japan (2008).

Supplementary European Search Report for EP Application No. 09 82 2192, The Hague, Netherlands, search completed on Nov. 22, 2012; 9 pages.

Deng, M.-D., et al., "Metabolic engineering of *Escherichia coli* for industrial production of glucosamine and N-acetylglucosamine," *Metab. Eng.* 7:201-214, elsevier Inc., Belgium (2005).

Tabata, K., et al., "Production of UDP-N-acetylglucosamine by coupling metabolically engineered bacteria," *Biotechnol. Lett.* 22:479-483, Kluwer Academic Publishers, Netherlands (2000).

English language abstract of Korean Patent Publication No. KR 10-2005-0053534 A.

English language abstract of Korean Patent Publication No. KR 10-2008-0025355 A.

International Preliminary Report on Patentability, including the Written Opinion of the International Searching Authority for International Application No. PCT/KR2009/006063, The International Bureau of WIPO, Geneva, Switzerland, issued May 31, 2011 (6 pages).

*Primary Examiner* — Kade Ariani
(74) *Attorney, Agent, or Firm* — Sterne, Kessler, Goldstein & Fox P.L.L.C.

(57) ABSTRACT

The present invention relates to a microorganism of the *Corynebacterium* genus that produces N-acetyl glucosamine which retains the activity of 6-phophate acetyltransferase and a method for producing N-acetyl glucosamine or glucosamine using the same.

9 Claims, 3 Drawing Sheets

CORYNEBACTERIUM GENUS MICROORGANISM HAVING ABILITY TO PRODUCE N-ACETYL GLUCOSAMINE AND METHOD FOR PRODUCING N-ACETYL GLUCOSAMINE OR GLUCOSAMINE USING THE SAME

REFERENCE TO SEQUENCE LISTING SUBMITTED ELECTRONICALLY VIA EFS-WEB

The content of the electronically submitted sequence listing (Name: 25110110001SequenceListing.txt; Size: 6,000 bytes; and Date of Creation: Jun. 1, 2011) is incorporated by reference in its entirety.

BACKGROUND OF THE INVENTION

1. Field of the Invention

The present invention relates to a genetically modified microorganism of the genus *Corynebacterium* producing N-acetal glucosamine, and a method for producing N-acetyl glucosamine or glucosamine using the same.

2. Description of the Related Art

Glucosamine is an amino derivative of glucose, and N-acetyl glucosamine is an acetylated derivative of glucosamine. They are important constituents of many natural polysaccharides, and can form structural materials for cells, constituting the cell wall.

N-acetyl glucosamine is an important component of protein synthesis, involved in tissue regeneration, and thus N-acetyl glucosamine has therapeutic potential in the prevention and treatment of a wide variety of diseases such as gastritis, food allergies, inflammatory bowel disease (IBD), diverticulitis, acute and chronic forms of rheumatoid arthritis and osteoarthritis, as well as the pathological conditions arising from metabolic disorders of the osteoarticular tissues. Glucosamine is also used as a functional food applied for the prevention, and treatment of human, osteoarthritic diseases.

Glucosamine is obtained by acid hydrolysis of chitin, a complex carbohydrate derived from N-acetyl glucosamine. Alternatively, glucosamine can also be produced by acid hydrolysis of chitosans. The raw material, chitin is a copolymer of N-acetyl glucosamine and glucosamine, and is a common natural substance found in arthropods and fungi. The chitin can be obtained from arthropod refuse (lobster, shrimp, krill, crab, and prawn exoskeletons) and more recently from inexpensive sources like fungal biomass used in citric acid production.

Common industrial practice is to purify the chitin by treating it with combinations of acids and bases to remove other impurities accompanying minerals, proteins, etc., and then to depolymerize and deacetylate the chitin in a single step into glucosamine through the use of concentrated hydrochloric acid in low yields at high temperature for a long time. Glucosamine as a free base is very unstable and subject to degradation. Consequently, stable salts such as hydrochloride are produced.

The glucosamine content in arthropod refuse and fungal biomass is low and thus large volumes of waste are produced. Glucosamine is considerably expensive because the production process itself has relatively low yield and is energy and chemically intensive. In addition, with the common forms of glucosamine, being derived from shellfish, it is known that there is the potential for allergic reactions in persons sensitive to shellfish. Moreover, the availability of raw material (e.g., a source of chitin, such as crab shells) becomes gradually limited. Therefore, there is a need for a cost-effective method for producing glucosamine and N-acetyl glucosamine in high yields for commercial sale and use.

PCT Publication No. WO 02/66667 discloses a method of making glucosamine from microbial biomass to remove the possibility of allergic reactions. This production method overcomes problems associated with shellfish allergy, but it suffers from a major problem of low yield. More particularly, since the method relies on the biomass waste generated in fermentation of other products such as citric acid, it is not enough to produce sufficient quantities of glucosamine that meet the increasing market demand for the product.

Meanwhile, N-acetyl glucosamine is currently produced by the acetylation of glucosamine using an organic acetylating reagent such as acetic anhydride, but this production method requires high costs. Also, because of low production yield, it is not easy to produce N-acetyl glucosamine on a large scale.

To overcome these problems, U.S. Pat. No. 7,332,304 discloses a method of producing N-acetyl glucosamine by *E. coli* fermentation. This method suggests *E. coli* fermentation for a high production yield of N-acetyl glucosamine which dramatically resolves the encountered problems including low production yield of N-acetyl glucosamine due to the conventional complicated process. In addition, it is known that glucosamine may be produced from deacetylation of N-acetyl glucosamine by simple acid treatment (Novikov V. Y. et al. Russ. J. Appl. Chem. 1997:1467-1470), and thus it is also possible to produce glucosamine in a high yield.

Figure 1:
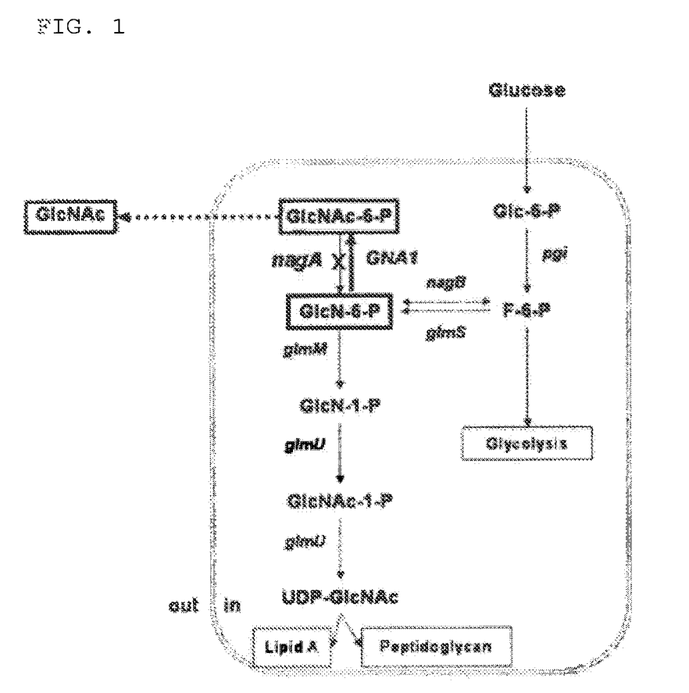
FIG. 1 illustrates N-acetyl glucosamine biosynthetic pathway and gene modification in N-acetyl glucosamine-producing strain, in which nagA is inactivated and a foreign gene GNA1 is amplified.

However, this method is not suitable for the production of health foods, because the use of *E. coli* generates potentially toxic endotoxins. In addition, glucosamine-6-phosphate acetyltransferase, essential for the production of N-acetyl glucosamine (see FIG. 1: GNA1), does not exist in *E. coli*, and thus other microorganisms such as yeast should be introduced. There is a limitation in that expression of the crucial enzyme requires an inducible expression system (Deng M. D. et al. Met Eng. 2005:201-214). Unregulated expression of the crucial enzyme causes severe inhibition of cell proliferation. The inducible expression system is disadvantageous in that an inducing material is needed, leading to an increase in production costs and an induction time point should be determined, and therefore it is considered to be not suitable for industrial production by large-scale fermentation. In terms of safety of production and possibility of industrial adaptation, the above method has a drawback of using *E. coli* and an inducible expression system.

Until now, *E. coli* fermentation technology has been developed in order to overcome the problems of the limited availability of raw materials and low production yield. However, there have been no strains, suitable for producing N-acetyl glucosamine and glucosamine, which are safe for humans and animals. Further, there have been no reports of a producing strain that utilizes a constitutive expression system other than an inducible expression system to facilitate industrial enzyme production.

In order to solve the above problems, the present inventors have developed a microorganism of the genus *Corynebacterium* for large-scale fermentation of N-acetyl glucosamine and glucosamine without causing environmental problems, capable of realizing production stability and industrial application, and a method for producing N-acetyl glucosamine and glucosamine using the same, thereby completing the present invention.

SUMMARY OF THE INVENTION

It is an object of the present invention to provide a genetically modified microorganism of the genus *Corynebacterium* producing N-acetyl glucosamine, and preferably a microorganism of the genus *Corynebacterium* having glucosamine-6-phosphate acetyltransferase activity and reduced or deleted glucosamine-6-phosphate deaminase activity.

It is another object of the present invention to provide a method for producing N-acetyl glucosamine or glucosamine using the microorganism of the genus *Corynebacterium*.

DETAILED DESCRIPTION OF THE PREFERRED EMBODIMENTS

In one aspect, the present invention relates to a microorganism of the genus *Corynebacterium* having an ability to produce N-acetyl glucosamine and glucosamine, in which the microorganism has a glucosamine-6-phosphate acetyltransferase activity and a reduced or deleted glucosamine-6-phosphate deaminase activity.

In the present invention, glucosamine-6-phosphate acetyltransferase refers to an enzyme for producing N-acetyl glucosamine-6-phosphate from the acetylation of glucosamine-6-phosphate. This enzyme is found in the microorganisms of the genus *Saccharomyces*, but not in the microorganisms of the genus *Corynebacterium*.

As used herein, the term "having a glucosamine-6-phosphate acetyltransferase activity" or "a microorganism of the genus *Corynebacterium* having a glucosamine-6-phosphate acetyltransferase activity" means that the glucosamine-6-phosphate acetyltransferase gene not present in the microorganisms of the genus *Corynebacterium* is introduced into a microorganism of the genus *Corynebacterium* to express glucosamine-6-phosphate acetyltransferase, and therefore, the microorganism of the genus *Corynebacterium* may convert N-glucosamine-6-phosphate into N-acetyl glucosamine-6-phosphate using the enzyme.

The method of imparting the glucosamine-6-phosphate acetyltransferase activity to the microorganism of the genus *Corynebacterium* by introduction of the gene may be performed by a variety of methods well known in the art. In the specific embodiment of the present invention, the glucosamine-6-phosphate acetyltransferase-encoding nucleic acid sequence is introduced into a vector, and the recombinant vector is used to transform the microorganism of the genus *Corynebacterium*.

The glucosamine-6-phosphate acetyltransferase gene is any gene that has a nucleic acid sequence being operable in the microorganism of the genus *Corynebacterium*. In one specific embodiment, the gene is a gene derived from *Saccharomyces cerevisiae*, and preferably a nucleic acid sequence of SEQ ID NO. 11. In particular, the glucosamine-6-phosphate acetyltransferase-encoding sequence can be modified to some degree as long as it retains its activity. It will be readily understood by those skilled in the art that the nucleic act sequence retaining 70% more homology by the artificial modification is equivalent to that derived from the nucleic acid sequence of the present invention, as long as it retains the gene activity desired in the present invention.

Preferably, a promoter is operably linked to the glucosamine-6-phosphate acetyltransferase gene of the present invention so as to induce expression of the gene. More preferably, with respect to the objects of the present invention, the promoter is a promoter to induce constitutive or inducible expression of glucosamine-6-phosphate acetyltransferase the microorganism of the genus *Corynebacterium*, and the promoter any gene that is able to induce constitutive or inducible expression of glucosamine-6-phosphate acetyltransferase introduced in the microorganism of the genus *Corynebacterium*. In one specific embodiment, the constitutive promoter is an EFTU promoter, and the inducible expression promoter is a laclq-Ptac promoter. When the expression of glucosamine-6-phosphate acetyltransferase in *E. coli* is induced at an early stage of growth, severe growth inhibition occurs, and thus an inducible expression system should be used only (Deng M. D. et al. Met Eng. 2005:201-214). On the contrary, the microorganism of the genus *Corynebacterium* of the present invention has an advantage that its growth is not affected by the inducible or constitutive expression of the enzyme.

As used herein, the term "glucosamine-6-phosphate deaminase" refers to an enzyme involved in the conversion of acetyl glucosamine-6-phosphate into glucosamine-6-phosphate. For the objects of the present invention, the microorganism of the genus *Corynebacterium* of the present invention is characterized in that it shows less or no expression of the glucosamine-6-phosphate deaminase-encoding gene, compared to the naturally occurring gene, due to partial or total deletion/mutation in the glucosamine-6-phosphate deaminase-encoding nucleic acid sequence. The lower or lack of expression of the glucosamine-6-phosphate deaminase-encoding gene, compared to the naturally occurring gene, due to partial or total deletion/mutation in the glucosamine 6-phosphate deaminase-encoding nucleic acid sequence can be expressed herein as "reduction" or "deletion".

To induce no or less expression of glucosamine-6-phosphate deaminase gene, for example, a mutation may occur in the promoter and regulatory regions located upstream of the structure gene. A regulatory cassette attached in upstream of the structural gene may also execute the same functions. The promoter may be modified to reduce the expression, or gene translation may be regulated by reduced m-RNA stability so as to reduce the expression. In addition, the activity of glucosamine-6-phosphate deaminase may be reduced or deleted by replacement of a part or the whole of the gene with a deleted or mutated fragment by site-specific recombination DNA technology. However, it is obvious to those skilled in the art that no or less expression of the gene may be achieved by a variety of methods well known in the art, in addition to these methods.

As used herein, the term "ability to produce N-acetyl glucosamine" means that the microorganism of the genus *Corynebacterium* of the present invention has an ability to produce and accumulate N-acetyl glucosamine in the media in which it is cultured. As used herein, the term "ability to produce glucosamine" refers to an ability to produce glucosamine from a material produced by microbial fermentation, and refers to an ability of the microorganism of the genus *Corynebacterium* of the present invention, that produces and accumulates glucosamine by deacetylation of N-acetyl glucosamine accumulated in the culture media into glucosamine, according to various methods known in the art.

As used herein, the term "microorganism having an ability to produce N-acetyl glucosamine and/or glucosamine" is a microorganism belonging to the genus *Corynebacterium*. Preferably, the microorganism is *Corynebacterium glutamicum* (e.g., ATCC13032), *Corynebacterium ammoniagenes* (e.g., ATCC 6872), *Brevibacterium lactofermentum* (e.g., ATCC13869), *Brevibacterium flavum* (e.g., ATCC14067), *Corynebacterium thermoaminogenes* (e.g., FERM-BP1539), *Corynebacterium efficiens* (e.g., *C. efficiens* str. YS-314) or the like, but is not limited thereto. More preferably, the microorganism is *Corynebacterium glutamicum*, and even more preferably, *Corynebacterium glutamicum* CJNAG1 deposited at KCCM (Korean Culture Center of Microorganisms, Eulim Buld., 361-221, Hongje-1-Dong, Seodaemun-Ku, Seoul, 120-861, Korea) on Sep. 29, 2008 with the Accession No: KCCM10967P.

In another aspect, the present invention relates to a method for producing N-acetyl glucosamine or glucosamine which comprises culturing the microorganism of the genus *Corynebacterium* having an ability to produce N-acetyl glucosamine.

In particular, the present invention relates to a method for producing N-acetyl glucosamine or glucosamine, comprising the steps of (a) culturing the microorganisms of the genus *Corynebacterium* having an ability to produce N-acetyl glucosamine of the present invention and (b) collecting N-acetyl glucosamine or glucosamine produced in the culturing step.

The above culture of the present invention can be performed by a proper medium and conditions known to those in the art. It is well understood by those in the art that the culture method can be used by easily adjusting the same, according to the selected strain. For example, the culture methods include, but are not limited to batch, continuous culture and fed-batch. A variety of culture methods are described in, for example, the following reference: "Biochemical Engineering" by James M. Lee, Prentice-Hall International Editions, pp 138-176. The medium used in the culture has to meet the culture conditions for a specific strain.

The medium used in the present invention contains glucose as a main carbon source, and the medium may contain a proper amount of various carbon sources. The nitrogen source to be used is exemplified by such organic nitrogen sources as peptone, yeast extract, gravy, malt extract, corn steep liquor and bean flour and such inorganic nitrogen source as urea, ammonium sulfate, ammonium chloride, ammonium phosphate, ammonium carbonate and ammonium nitrate. These nitrogen sources may be used either alone or in combinations. The medium herein can additionally include potassium dihydrogen phosphate, dipotassium hydrogen phosphate and corresponding sodium-containing salts as a phosphate source. The medium also can include a metal salt such as magnesium sulfate or iron sulfate. In addition, amino acids, vitamins and proper precursors can be added. These mediums or precursors can be added to the culture by batch-type or continuous type.

During cultivation, ammonium hydroxide, potassium hydroxide, ammonia, phosphoric acid, and sulfuric acid may be properly added so as to adjust the pH of the cultures. Defoaming agents such as fatty acid polyglycol ester may he properly added so as to reduce the formation of foams in cultures. To maintain the cultures in aerobic states, oxygen or oxygen-containing gas may be injected into the cultures. To maintain the cultures in anaerobic and microaerobic states, no gas may be injected or nitrogen, hydrogen, or carbon dioxide gas may be injected into the cultures. The cultures are maintained at 30 to 37° C., and preferably at 35 to 37° C.. The cultivation may be continued until a desired amount of the desired material is obtained, and preferably for 10 to 160 hrs.

The step of collecting and/or recovering N-acetyl glucosamine or glucosamine produced in the cultivation step of the present invention may be performed by a proper method known in the art, depending on the culturing procedures, for example, batch type, continuous type or fed-batch type, so as to collect the desired N-acetyl glucosamine or glucosamine from the culture medium.

In addition, the present invention may further include the step of converting the collected N-acetyl glucosamine into glucosamine by deacetylation. It will be apparent to those skilled in the art that the conversion may be performed by the method widely known in the art (e.g., Novikov V. Y. et al. Russ. J. Appl. Chem. 1997:1467-1470).

Hereinafter, the present invention will be described in more detail with reference to Examples. However, these Examples are for illustrative purposes only, and the invention is not intended to be limited by these Examples.

EXAMPLE 1

Construction of N-acetyl glucosamine 6-phosphate Deaminase Mutant and Chromosomal DNA Substitution Recombinant Vector pDZ-nagAST To prevent utilization of N-acetyl glucosamine-6-phosphate by the wild-type *Corynebacterium glutamicum* (ATCC13102), N-acetyl glucosamine-6-phosphate deaminase-encoding nagA1 (NCgl2556, SEQ ID NO. 1) which utilizes N-acetyl glucosamine-6-phosphate as a substrate was inactivated.

The inactivation may be performed by various methods such as gene deletion or introduction of additional sequence, and in the present Example, a stop codon was inserted into the ORF (open reading frame) of the nagA1 gene to induce inactivation of gene translation.

Specifically, a genomic DNA was isolated from *Corynebacterium glutamicum* (ATCC13102), and PCR was performed using the genomic DNA as a template and primers of SEQ ID NOs. 2 and 3 so as to obtain N-acetyl glucosamine-6-phosphate deaminase-encoding gene (nagA1: NCgl2556).

Each sequence of the primers used to amplify nagA1 gene is as follows.

```
SEQ ID NO. 2 (nagA1-5)
5'-GGAATTCATGGCAGAAGTGGTGCATTATCAAG-3'

SEQ ID NO. 3 (nagA1-3)
5'-GCTCTAGAGATGATGTCCATGGTCGGACTCC-3'
```

To construct an N-acetyl glucosamine-6-phosphate deaminase mutant having a stop codon in ORF using the wild-type N-acetyl glucosamine-6-phosphate deaminase gene, additional primers (SEQ ID NOs. 4 and 5) were prepared to insert a stop codon between isoleucine at position 196 and alanine at position 197.

Figure 2:
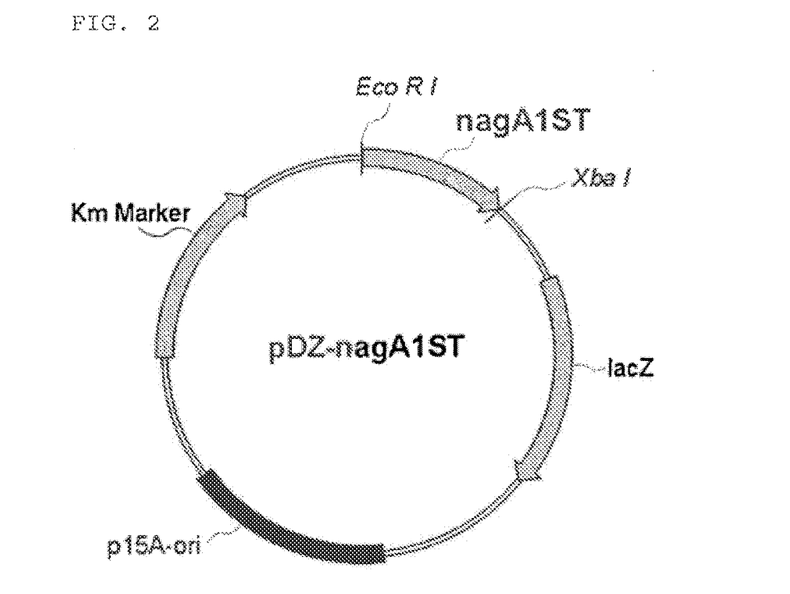
FIG. 2 illustrates a structure of pDZ-nagA1ST vector, in which nagA1 having a stop codon is cloned into PDZ.

Specifically, PCR was performed using the wild-type nagA1 obtained by PCR as a template and each of the primers of SEQ ID NOs. 2 and 4 and SEQ ID NOs. 3 and 5. Two final products were a part of the nagA1, and thus had a half size thereof. These two products were simultaneously used as a template and the primers of SEQ ID NOs. 2 and 3 were used to perform PCR again. Through this procedure, genes encoding inactivated N-acetyl glucosamine 6-phosphate deaminase mutants were obtained. The inactivated nagA1 gene fragment was introduced into a chromosomal DNA substitution vector pDZ using the restriction enzymes, EcoRI (New England Biolabs, Beverly, Mass.) and XbaI (New England Biolabs, Beverly, Mass.) by the molecular biology technique disclosed in Korean Patent Publication No. 2008-0025355, so as to construct. a pDZ-nagA1ST vector (FIG. 2).

```
SEQ ID NO. 4 (magA1ST-5)
5'-CTGCCCGAAGGAAGCTTAATGATGTGGTGCGC-3'

SEQ ID NO. 5 (nagA1ST-3)
5'-GCGCACCACATCATTTAAGCTTCCTTCGGGCAC-3'
```

EXAMPLE 2

Construction of *Corynebacterium glutamicum* CJNAGKO

To transform the wild type *Corynebacterium glutamicum* (ATCC13102) strain with the constructed pDZ-nagA1ST vector, a stop codon was inserted into the ORF of nagA1 gene on the chromosome by secondary crossover, as described in Korean Patent Publication No. 2008-0025355. Finally, a stop codon was inserted between isoleucine at position 196 and alanine at position 197 to construct CJNAGKO.

EXAMPLE 3

Construction of Constitutive Expression Vector of Glucosamine-6-phosphate Acetyltransferase In order to produce N-acetyl glucosamine, a vector expressing glucosamine-6-phosphate acetyltransferase, which is an enzyme producing N-acetyl glucosamine-6-phosphate using glucosamine-6-phosphate as a substrate, was constructed. For industrial application, a constitutive promoter was used to construct the vector so as to ensure constitutive expression of the enzyme during cell growth. The enzyme used for the expression was GNA1, the known glucosamine-6-phosphate acetyltransferase gene of yeast *Saccharomyces cerevisiae*.

Figure 3:
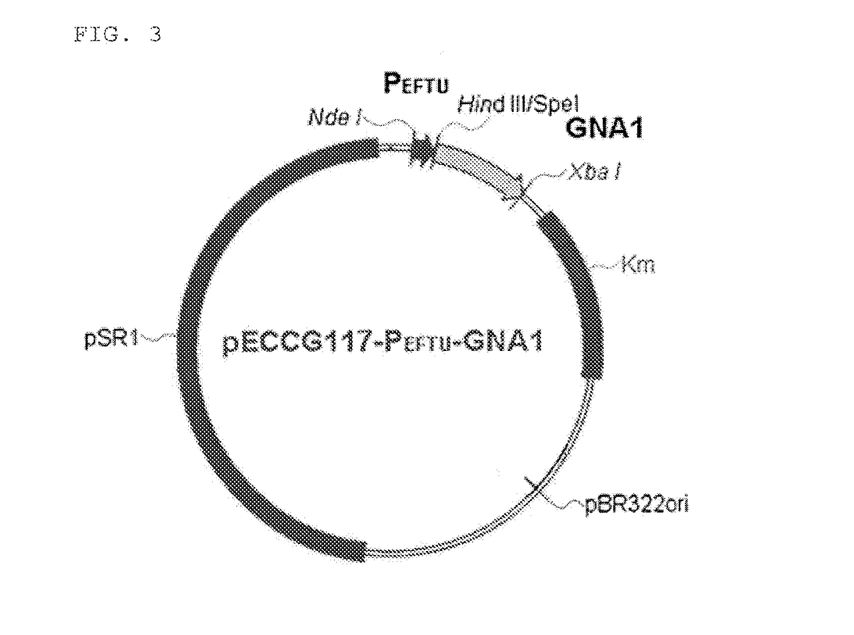
FIG. 3 illustrates a structure of pECCG117-PEFTU-GNA1 vector, in which the constitutive expression promoter PEFTU is primarily cloned into a pECCG117 vector, and GNA1 is additionally cloned thereto.

For constitutive expression of the enzyme, an EFTU promoter (Judith B. et al., Appl Environ Microbiol. 2005:8587-8596.) that is known as a constitutive promoter in *Corynebacterium glutamicum* was used. PCR was performed using the chromosome isolated from *Corynebacterium glutamicum* as a template and the primers of SEQ ID NOs. 6 and 7 to obtain the EFTU promoter (SEQ ID NO. 8). The obtained PCR product of EFTU promoter was introduced into a pECCG1117 vector (Biotechnology letters vol 13. No.10, p.721-726 (1991) or Korean Patent Publication No. 92-7401) using the restriction enzymes, NdeI (New England Biolabs, Beverly, Mass.) and HindIII (New England Biolabs, Beverly, Mass.) by the known molecular biology technique. The constructed vector was designated pECCG117-PEFTU. In addition, PCR was performed using the chromosome isolated from *Saccharomyces cerevisiae* as a template and the primers of SEQ ID NOs. 9 and 10 to obtain GNA1 (SEQ ID NO. 11). The obtained GNA1 was introduced into the pECCG117-PEFTU vector using SpeI (New England Biolabs, Beverly, Mass.) and XbaI (New England Biolabs, Beverly, Mass.) to construct a pECCG117-PEFTU-GNA1 vector (FIG. 3).

Each sequence of the primers used to amplify the EFTU promoter and GNA1 gene is as follows.

SEQ ID NO. 6 (EFTU-5)
5'-GACTAGTATGTTCGGTTACGTCGGTGACCTTC-3'
SEQ ID NO. 7 (EFTU 3)
5'-CCCAAGCTTCTATTTTCTAATTTG-CATTTCCACGCCTGC-3'
SEQ ID NO. 9 (GNA1-5)
5'-GGAATTCCATATGAGCTTACCCGATG-GATTTTATATAAGG-3'
SEQ ID NO. 10 (GNA1-3)
5'-GCTCTAGACTATTTTCTAATTTG-CATTTCCACGCC-3'

EXAMPLE 4

Construction of Inducible Expression Vector of Glucosamine-6-phosphate Acetyltransferase An inducible expression system of *Corynebacterium glutamicum* was constructed to compare with the constitutive expression system of *Corynebacterium glutamicum* of Example 3.

Figure 4:
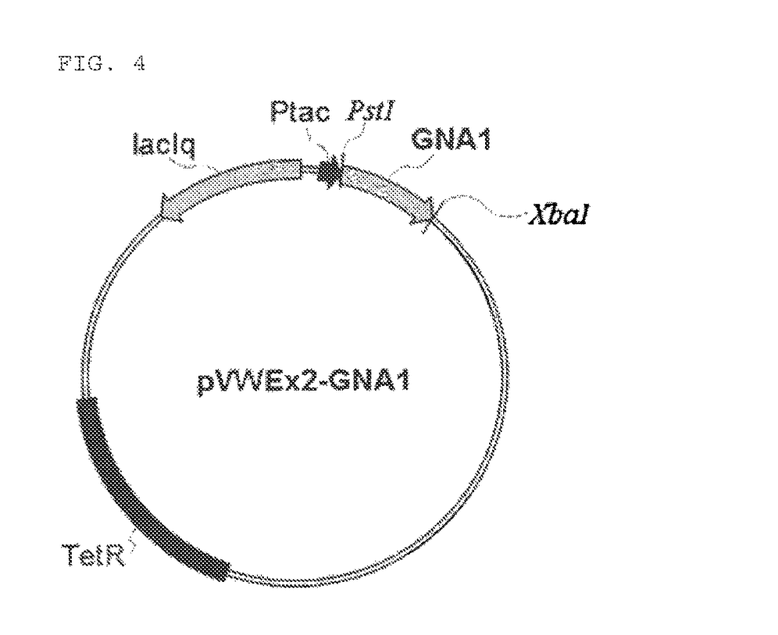
FIG. 4 illustrates a structure of pVWEx2-GNA1 vector, in which GNA1 is cloned into a pVWEx2 vector.

Specifically, PCR was performed using the chromosome isolated from *Saccharomyces cerevisiae* as a template and the primers of SEQ. ID NOs. 9 and 10 to obtain GNA1. The obtained GNA1 was introduced into a pVWEx2 vector known as an inducible expression system in *Corynebacterium glutamicum* (Appl. Microbiol. Biotechnol. 2007, 76:545-552) using PstI (New England Biolabs, Beverly, Mass.) and XbaI (New England Biolabs, Beverly, Mass.) to construct a pVWEx2-GNA1 vector (FIG. 4). A lacIq-Ptac promoter was used for the inducible expression. Each sequence of the used primers is as follows.

```
SEQ ID NO. 12 (Vw2-GNA1-5)
5'-AACTGCAGATGAGCTTACCCGATGGATTTTATATAAGG-3'

SEQ ID NO. 13 (Vw2-GNA1-3)
5'-GCTCTAGACTATTTTCTAATTTGCATTTCCACGCCTGC-3'
```

EXAMPLE 5

Production of N-acetyl Glucosamine Using GNA1-introduced *Corynebacterium glutamicum* CJNAGKO In order to produce N-acetyl glucosamine using *Corynebacterium glutamicum*, glucosamine-6-phosphate acetyltransferase (GNA1) was introduced into the mutant CJNAGKO which has a stop codon in the N-acetyl glucosamine-6-phosphate deaminase (nagA1) ORF on the chromosome, That is, each of p117-PEFTU-GNA1 and pVWEx2-GNA1 constructed in Examples 3 and 4 was transformed into CJNAGKO to prepare strains that have a glucosamine-6-phosphate acetyltransferase (GNA1) activity without N-acetyl glucosamine-6-phosphate deaminase activity. The prepared strains are designated CJNAG1 (KCCM10967P) and CJNAG2, respectively (Table 1).

In order to test whether the prepared strains produce N-acetyl glucosamine, a strain having inactivated N-acetyl glucosamine-6-phosphate deaminase only (Control 2) and a strain having amplified glucosamine-6-phosphate acetyltransferase only (Control 3) were prepared and used as control groups. The wild-type *Corynebacterium glutamicum* was also used as a control group (Control 1). Finally, the production of N-acetyl glucosamine was analyzed (Table 1).

The medium composition and culture method were as follows. 5 ml of seed medium (5 q of trypton, 2.5 g of yeast extract, 5 g of NaCl, 18.5 g of Brain heart infusion in 500 ml of distilled water, and 91 g of sorbitol in 500 ml of distilled water, each of them were sterilized at high pressure and high temperature, and then mixed with each other) was put in test tubes, and then test strains were inoculated thereto, followed by incubation at 30° C. for 12 hrs. 20 ml of the culture media (based on 1 L of distilled water, 90 g of glucose sterilized separately, 40 g of $(NH_4)_2SO_4$, 2.5 g of Soy Protein, 5 g of Corn Steep Solids, 3 g of urea, 1 g of $KH_2PO_4$, 0.5 g of $MgSO_4\cdot 7H_2O$, 100 μg of biotin, 1000 μg of thiamine hydrochloride, 2000 μg of calcium pantothenate, 3000 μg of nicotinamide, 30 g of $CaCO_3$ sterilized separately) was aliquoted in 250 ml Erlenmeyer flasks, and then 200 μl of seed culture medium was inoculated thereto, followed by fermentation at 30° C. for 42 hrs. In particular, 100 μM of IPTG was added to 'Control 3' and 'CJNAG2' that were transformed with pVWEx2-GNA1, when optical density (OD) of the cells was 1.0 at 600 nm. Each strain was tested using three flasks, and the average number of cells and N-acetyl glucosamine concentration were measured. The fermentation results showed that N-acetyl glucosamine was produced at a concentration of approximately 1.0 g/L or more, irrespective of constitutive and inducible expression (Table 1). It can be seen that the constitutive expression system can be additionally used in the *Corynebacterium*, whereas the known NAG production by the use of *E. coli* should adopt only the inducible expression system that allows for the separation of the growth and production phase.

TABLE 1

| Strain | | Cell OD (Abs. 600 nm) | N-acetyl glucosamine (mg/L) |
|---|---|---|---|
| Control 1 | Wild-type strain | 87.2 | 42 |
| Control 2 | nagA1-inactivated strain | 81.1 | 44 |
| Control 3 | GNA1 inducible expression strain | 82.3 | 50 |
| CJNAG1 | nagA1-inactivated and GNA1 constitutive expression strain | 88.1 | 1,241 |
| CJNAG2 | nagA1-inactivated and GNA1 inducible expression strain | 83.3 | 1,108 |

Glucosamine can be produced from deacetylation of the produced N-acetyl glucosamine by acid treatment, which can be performed by the known method described in Novikov V. Y. et al. (Russ. J. Appl. Chem. 1997;1467-1470), indicating that the production of N-acetyl glucosamine easily allows additional production of glucosamine.

Various modifications or variations of the invention in addition to those shown and described herein will become apparent to those skilled in the art from the foregoing description. Such modifications and variations are intended to fall within the scope of the claims appended hereto.

Effect of the Invention

According to the present invention, a microorganism of the genus *Corynebacterium* having an ability to produce N-acetyl glucosamine can be developed, and thus N-acetyl glucosamine or glucosamine produced using the microorganism, thereby realizing mass production of N-acetyl glucosamine and glucosamine without the risk of allergic reactions. Further, it is industrially applicable, since health foods and therapeutic materials can safely produced, and crucial enzymes can be constitutively expressed.

What is claimed is:

1. A genetically modified microorganism of the genus *Corynebacterium* having an ability to produce N-acetyl glucosamine, wherein the microorganism is modified to have a glucosamine-6-phosphate acetyltransferase activity by introducing a gene encoding glucosamine-6-phosphate acetyltransferase, and wherein the microorganism is further modified to have a reduced or deleted glucosamine-6-phosphate deaminase activity.

2. The microorganism according to claim 1, wherein the glucosamine-6-phosphate acetyltransferase is encoded by a nucleic acid molecule that comprises the nucleotide sequence of SEQ ID NO. 11.

3. The microorganism according to claim 1, wherein the glucosamine-6-phosphate acetyltransferase is inducibly or constitutively expressed.

4. The microorganism according to claim 3, wherein the constitutive expression is driven by an EFTU promoter.

5. The microorganism according to claim 3, wherein the inducible expression is driven by a lacIq-Ptac promoter.

6. The microorganism according to claim 1, wherein the microorganism is *Corynebacierium glutamicum*.

7. The microorganism according to claim 1, wherein the microorganism is *Corynebacterium glutamicum* CJNAG1 (KCCM10967P).

8. A method for producing N-acetyl glucosamine comprising:
   (a) culturing the microorganisms of any one of claims 1 to 7 under conditions suitable to produce N-acetyl-glucosamine, and
   (b) collecting N-acetyl glucosamine.

9. The method according to claim 8, further comprising deacetylation of the collected N-acetyl glucosamine.

* * * * *

SEQUENCE LISTING

```
<160> NUMBER OF SEQ ID NOS: 13

<210> SEQ ID NO 1
<211> LENGTH: 1167
<212> TYPE: DNA
<213> ORGANISM: Corynebacterium glutamicum
<220> FEATURE:
<221> NAME/KEY: gene
<222> LOCATION: (1)..(1167)
<223> OTHER INFORMATION: nagA1(NCgl2556)

<400> SEQUENCE: 1
atggcagaag tggtgcatta tcaagaaaat gcaggtcaag cagttaaaaa aattgaagga      60
agaattgtta cccccacgg ggtgattgat ggctttctcc aactcgaaaa cggcatcatc     120
acggaactct ctggagaacc agcacctaaa aacgcaggat tccaccccga actccccacg     180
attgttccca gttttattga tcttcataat cacggtggaa acggtggcgc gtttcctacg     240
ggaacgcagg accaggcgag gaatgccgcg cagtatcacc gcgaacatgg cacgaccgtg     300
atgttggcaa gcatggtttc ggcgccggct gacgcactgg cagcgcaggt ggaaaaacctt     360 attcccttgt gtgaagaggg cctgctgtgc ggcattcacc tcgagggtcc tttcatcaac     420
```

```
gcatgccgtt gtggtgctca aaacccggat tttattttc ccggcaaccc aacagatctt    480
gcccaggtga tccatgcggg aaaaggttgg atcaaatcga tcacagtagc gccggaaact    540
gacaatctta ctgagcttct cgatctctgc gcagcgcacc acatcattgc ttccttcggg    600
cacactgatg cagattttga taccactacc agcgcaattg ccttggctaa agagaaaaat    660
gtgacggtca cggctacgca tttgttcaat gcgatgcctc cgctgcatca tagggatccc    720
ggcagcgtgg gcgctttgct tgctgcggca cgtgccgggg acgcatatgt tgagttgatc    780
gccgacggcg tgcatttggc cgatggaacg gtcgatctag ctcgttccaa caacgccttt    840
ttcatcacgg acgccatgga agccgccgga atgccagacg tgagtacat tttgggcgtt     900 ttgaacgtca ccgtcaccga tggcgtcgcc cgtctgcgcg atggcggcgc catcgccggg    960
ggtaccagca cactagcgag tcagttcgtg caccacgtgc gcaggggtat gacgcttatc    1020
gacgcgaccc tccacacctc aaccgtcgcc gccaaaattc tcggacttag cgatcacgaa    1080
atcgttaaat ccaaccctgt aaattttgtg gtctttgact caaacggcca gttacaacag    1140
gtccatttag accatcaagt aatttaa                                        1167

<210> SEQ ID NO 2
<211> LENGTH: 32
<212> TYPE: DNA
<213> ORGANISM: Artificial Sequence
<220> FEATURE:
<223> OTHER INFORMATION: forward primer for amplication of nagA1

<400> SEQUENCE: 2
ggaattcatg gcagaagtgg tgcattatca ag                                  32

<210> SEQ ID NO 3
<211> LENGTH: 31
<212> TYPE: DNA
<213> ORGANISM: Artificial Sequence
<220> FEATURE:
<223> OTHER INFORMATION: reverse primer for amplification of nagA1

<400> SEQUENCE: 3
gctctagaga tgatgtccat ggtcggactc c                                   31

<210> SEQ ID NO 4
<211> LENGTH: 33
<212> TYPE: DNA
<213> ORGANISM: Artificial Sequence
<220> FEATURE:
<223> OTHER INFORMATION: forward primer for amplication of mutated nagA1

<400> SEQUENCE: 4
gtgcccgaag gaagcttaaa tgatgtggtg cgc                                 33

<210> SEQ ID NO 5
<211> LENGTH: 33
<212> TYPE: DNA
<213> ORGANISM: Artificial Sequence
<220> FEATURE:
<223> OTHER INFORMATION: reverse primer for amplification of mutated
      nagA1

<400> SEQUENCE: 5
gcgcaccaca tcatttaagc ttccttcggg cac                                 33

<210> SEQ ID NO 6
<211> LENGTH: 32
```

```
<212> TYPE: DNA
<213> ORGANISM: Artificial Sequence
<220> FEATURE:
<223> OTHER INFORMATION: forward primer for amplification of EFTU
      promoter

<400> SEQUENCE: 6
gactagtatg ttcggttacg tcggtgacct tc                                   32

<210> SEQ ID NO 7
<211> LENGTH: 39
<212> TYPE: DNA
<213> ORGANISM: Artificial Sequence
<220> FEATURE:
<223> OTHER INFORMATION: reverse primer for amplification of EFTU
      promoter

<400> SEQUENCE: 7
cccaagcttc tattttctaa tttgcatttc cacgcctgc                            39

<210> SEQ ID NO 8
<211> LENGTH: 497
<212> TYPE: DNA
<213> ORGANISM: Corynebacterium glutamicum
<220> FEATURE:
<221> NAME/KEY: promoter
<222> LOCATION: (1)..(497)
<223> OTHER INFORMATION: EFTU promoter

<400> SEQUENCE: 8
atgttcggtt acgtcggtga ccttcgctct aagacccagg gtcgtgcaaa ctactccatg     60
gtcttcgatt cctacgctga ggtcccagcc aacgttgccg cagatgttat tgctgagcgc   120
aacggcaccg cttcctaaag atcgtttaga tccgaaggaa aacgtcgaaa agcaatttgc   180
ttttcgacgc cccaccccgc gcgttttagc gtgtcagtag gcgcgtaggg taagtggggt   240
agcggcttgt tagatatctt gaaatcggct ttcaacagca ttgatttcga tgtatttagc   300
tggccgttac cctgcgaatg tccacagggt agctggtagt ttgaaaatca acgccgttgc   360
ccttaggatt cagtaactgg cacattttgt aatgcgctag atctgtgtgc tcagtcttcc   420
aggctgctta tcacagtgaa agcaaaacca attcgtggct gcgaaagtcg tagccaccac   480
gaagtccagg aggacat                                                  497

<210> SEQ ID NO 9
<211> LENGTH: 40
<212> TYPE: DNA
<213> ORGANISM: Artificial Sequence
<220> FEATURE:
<223> OTHER INFORMATION: forward primer for amplification of GNA1

<400> SEQUENCE: 9
ggaattccat atgagcttac ccgatggatt ttatataagg                           40

<210> SEQ ID NO 10
<211> LENGTH: 35
<212> TYPE: DNA
<213> ORGANISM: Artificial Sequence
<220> FEATURE:
<223> OTHER INFORMATION: reverse primer for amplification of GNA1

<400> SEQUENCE: 10
gctctagact attttctaat ttgcatttcc acgcc                                35

<210> SEQ ID NO 11
```

```
<211> LENGTH: 480
<212> TYPE: DNA
<213> ORGANISM: Saccharomyces cerevisiae
<220> FEATURE:
<221> NAME/KEY: gene
<222> LOCATION: (1)..(480)
<223> OTHER INFORMATION: GNA1

<400> SEQUENCE: 11
atgagcttac ccgatggatt ttatataagg cgaatggaag aggggatttt ggaacaggtc      60
actgagacgc taaaggtttt gaccaccgtg ggcactatta cccccgaatc cttcagcaaa     120
ctcataaaat actggaatga agccacagta tggaatgata acgaagataa aaaaataatg     180
caatataacc ccatggtgat tgtggacaag cgcaccgaga cggttgccgc tacggggaat     240
atcatcatcg aaagaaagat cattcatgaa ctggggctat gtggccacat cgaggacatt     300
gcagtaaact ccaagtatca gggccaaggt ttgggcaagc tcttgattga tcaattggta     360
actatcggct ttgactacgg ttgttataag attattttag attgcgatga gaaaaatgtc     420
aaattctatg aaaaatgtgg gtttagcaac gcaggcgtgg aaatgcaaat tagaaaatag     480

<210> SEQ ID NO 12
<211> LENGTH: 38
<212> TYPE: DNA
<213> ORGANISM: Artificial Sequence
<220> FEATURE:
<223> OTHER INFORMATION: forward primer for amplification of Vw2-GNA1

<400> SEQUENCE: 12
aactgcagat gagcttaccc gatggatttt atataagg                              38

<210> SEQ ID NO 13
<211> LENGTH: 38
<212> TYPE: DNA
<213> ORGANISM: Artificial Sequence
<220> FEATURE:
<223> OTHER INFORMATION: reverse primer for amplification of Vw2-GNA1

<400> SEQUENCE: 13
gctctagact attttctaat ttgcatttcc acgcctgc                              38
```